United States Patent
Horiike

(10) Patent No.: US 11,134,922 B2
(45) Date of Patent: Oct. 5, 2021

(54) IMAGING APPARATUS FOR DIAGNOSIS

(71) Applicant: TERUMO KABUSHIKI KAISHA, Tokyo (JP)

(72) Inventor: Toyokazu Horiike, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 527 days.

(21) Appl. No.: 15/915,206

(22) Filed: Mar. 8, 2018

(65) Prior Publication Data

US 2018/0271497 A1 Sep. 27, 2018

(30) Foreign Application Priority Data

Mar. 22, 2017 (JP) .............................. JP2017-056436

(51) Int. Cl.
*A61B 8/08* (2006.01)
*A61B 8/12* (2006.01)
(Continued)

(52) U.S. Cl.
CPC .......... *A61B 8/5261* (2013.01); *A61B 5/0035* (2013.01); *A61B 5/0066* (2013.01);
(Continued)

(58) Field of Classification Search
CPC ........... A61B 8/08; A61B 8/5261; A61B 8/56; A61B 5/0066; A61B 8/4416;
(Continued)

(56) References Cited

U.S. PATENT DOCUMENTS

2004/0111029 A1* 6/2004 Bates .................. A61B 8/4281
600/437
2004/0234206 A1* 11/2004 Hamm ................ A61B 5/6852
385/53
(Continued)

FOREIGN PATENT DOCUMENTS

EP 2 484 288 A1 8/2012
EP 3 120 749 A1 1/2017
(Continued)

OTHER PUBLICATIONS

Extended European Search Report dated Jun. 25, 2018, by the European Patent Office in corresponding European Patent Application No. 18162985.8—1124. (8 pages).

*Primary Examiner* — Oommen Jacob
(74) *Attorney, Agent, or Firm* — Buchanan Ingersoll & Rooney PC

(57) ABSTRACT

A technique is disclosed for downsizing a motor drive unit (MDU) and improving durability in an imaging apparatus for diagnosis. In the motor drive unit, when a catheter connector is connected, a motor drive unit connector (MDU connector) for being connected to the catheter connector has a shape which accommodates the catheter connector in order to optically connect an optical fiber of a cylindrical member of a catheter and an optical fiber leading from the imaging apparatus for diagnosis to each other, and in order to connect an electrical contact portion of the catheter and an optical/electrical signal line leading from the imaging apparatus for diagnosis to each other. Then, the motor drive unit has a structure, which supports a center position of an end portion
(Continued)

of the optical fiber exposed from the cylindrical member of the catheter, as a rotation center position of an imaging core.

5 Claims, 4 Drawing Sheets

(51) Int. Cl.
    *A61B 5/00*            (2006.01)
    *A61B 8/00*            (2006.01)

(52) U.S. Cl.
    CPC .......... *A61B 5/0073* (2013.01); *A61B 5/0084* (2013.01); *A61B 8/12* (2013.01); *A61B 8/4416* (2013.01); *A61B 8/4461* (2013.01); *A61B 8/56* (2013.01); *A61B 2562/227* (2013.01); *A61B 2562/228* (2013.01)

(58) Field of Classification Search
    CPC ....... A61B 5/0073; A61B 5/0084; A61B 8/12; A61B 5/0035; A61B 8/4461; A61B 2562/227; A61B 2562/228; A61B 5/0006; A61B 5/6852–6859; A61B 1/00112–00128
    USPC ......................................... 600/427, 424, 407
    See application file for complete search history.

(56) References Cited

U.S. PATENT DOCUMENTS

| | | | |
|---|---|---|---|
| 2006/0147158 A1* | 7/2006 | Sato | G02B 6/4204 385/78 |
| 2007/0282197 A1* | 12/2007 | Bill | A61B 5/062 600/424 |
| 2008/0161696 A1* | 7/2008 | Schmitt | A61B 5/0066 600/467 |
| 2008/0177183 A1* | 7/2008 | Courtney | A61B 8/12 600/463 |
| 2009/0043191 A1* | 2/2009 | Castella | A61B 5/6852 600/425 |
| 2010/0094109 A1* | 4/2010 | Tang | A61B 5/1459 600/341 |
| 2011/0098572 A1* | 4/2011 | Chen | A61B 5/0066 600/463 |
| 2012/0002928 A1* | 1/2012 | Irisawa | G02B 6/3891 385/92 |
| 2018/0271497 A1* | 9/2018 | Horiike | A61B 8/5261 |

FOREIGN PATENT DOCUMENTS

| | | |
|---|---|---|
| JP | H11-056752 A | 3/1999 |
| JP | 2006-204430 A | 8/2006 |
| WO | 2015/141136 A1 | 9/2015 |

* cited by examiner

IMAGING APPARATUS FOR DIAGNOSIS

CROSS-REFERENCES TO RELATED APPLICATIONS

This application claims priority to Japanese Application No. 2017-056436 filed on Mar. 22, 2017, the entire content of which is incorporated herein by reference.

TECHNICAL FIELD

The present disclosure relates to an imaging apparatus for diagnosis using a catheter.

BACKGROUND

As an apparatus for diagnosing a vascular lumen, an intravascular ultra sound (IVUS) apparatus and an optical coherence tomography (OCT) apparatus are known.

An ultrasound wave has a property in which the ultrasound wave reaches a relatively deep site of a vascular tissue. Accordingly, a vascular tomographic image obtained using the IVUS is suitably used in order to diagnosing not only a surface of the vascular tissue but also the deep site. On the other hand, light does not reach a deep tissue compared to the ultrasound wave. However, an intravascular wall image having extremely high resolution can be obtained compared to that of IVUS.

The configuration is adopted as described above. Accordingly, the following imaging apparatus for diagnosis has recently been proposed. In the imaging apparatus for diagnosis, a catheter, which accommodates both an ultrasound transceiver and an optical transceiver, that is, a hybrid type catheter is used so as to generate both images of an ultrasound tomographic image and an optical tomographic image (JP-A-11-56752 and JP-A-2006-204430).

In a case of using this type apparatus, the catheter is connected to a motor drive unit for rotating and moving an internally provided imaging core.

In addition, a length of the catheter is limited. Accordingly, since the motor drive unit is inevitably installed closer to a patient during a medical procedure, it is preferable that the motor drive unit is downsized as much as possible.

In addition, since the catheter is repeatedly attached to and detached from the motor drive unit in accordance with the medical procedure, it can also be desirable that the motor drive unit has improved durability.

SUMMARY

An imaging apparatus is disclosed for diagnosis in which a motor drive unit is downsized and durability is improved.

In accordance with an exemplary embodiment, the imaging apparatus for diagnosis according to the present disclosure has the following configurations.

That is, there is provided an imaging apparatus for diagnosis which has a motor drive unit (MDU) for being connected to a catheter and for moving and rotating an imaging core accommodated in the catheter along a longitudinal direction of the catheter, and which generates a vascular optical coherence tomographic image and an ultrasound tomographic image of a subject, based on a signal output from the catheter. A catheter connector for being connected to the MDU in the catheter has a first cylindrical member that accommodates an optical fiber optically connected to an optical transceiver disposed in a distal end of the imaging core, and that holds the optical fiber while exposing an end portion of the optical fiber, a cylindrical-shaped second cylindrical member that is fixed to the first cylindrical member, and that has a plurality of connection terminals electrically connected to an ultrasound transceiver disposed in the distal end of the imaging core, and a connector unit that rotatably supports the first and second cylindrical members. An MDU connector for being connected to the catheter connector in the MDU has a shape which accommodates the catheter connector in order to optically connect an optical fiber of the first cylindrical member and an optical fiber leading from the imaging apparatus for diagnosis to each other when the catheter connector is connected, and in order to connect an electrical contact portion and an optical/electrical signal line leading from the imaging apparatus for diagnosis to each other. The MDU supports a center position of the end portion of the optical fiber exposed from the first cylindrical member of the catheter, as a rotation center position of the imaging core.

An imaging apparatus for diagnosis is disclosed, the imaging apparatus comprising: a motor drive unit (MDU) configured to be connected to a catheter and configured to move and rotate an imaging core accommodated in the catheter along a longitudinal direction of the catheter, and to generate a vascular optical coherence tomographic image and an ultrasound tomographic image of a subject, based on a signal output from the catheter; a catheter connector configured to be connected to the MDU in the catheter has a first cylindrical member that accommodates an optical fiber optically connected to an optical transceiver disposed in a distal end of the imaging core, and that holds the optical fiber while exposing an end portion of the optical fiber, a cylindrical-shaped second cylindrical member that is fixed to the first cylindrical member, and that has a plurality of connection terminals electrically connected to an ultrasound transceiver disposed in the distal end of the imaging core, and a connector unit that rotatably supports the first and second cylindrical members; and wherein when the catheter connector is connected, a MDU connector configured to be connected to the catheter connector in the MDU has a first hollow cylindrical portion which optically connects an optical fiber of the first cylindrical member and an optical fiber leading from the imaging apparatus for diagnosis to each other, and a second hollow cylindrical portion which has an electrode configured to be connected to the connection terminal of the second cylindrical member and which has an opening portion for accommodating the first hollow cylindrical portion, and wherein the first hollow cylindrical portion is attachable to and detachable from the second hollow cylindrical portion.

A catheter is disclosed, the catheter comprising: a catheter connector configured to be connected to a motor drive unit (MDU) of an imaging apparatus for diagnosis, the MDU configured to move and rotate an imaging core accommodated in the catheter along a longitudinal direction of the catheter, and to generate a vascular optical coherence tomographic image and an ultrasound tomographic image of a subject, based on a signal output from the catheter, wherein the catheter connector has a first cylindrical member that accommodates an optical fiber optically connected to an optical transceiver disposed in a distal end of the imaging core, and that exposes and holds an end portion of the optical fiber, a cylindrical-shaped second cylindrical member that is fixed to the first cylindrical member, and that has a plurality of connection terminals electrically connected to an ultrasound transceiver disposed in the distal end of the imaging core, and a connector unit that rotatably supports the first and second cylindrical members, and wherein the first cylindrical member is provided with a projection portion for regulating a rotation direction.

According to the present disclosure, an imaging apparatus for diagnosis is disclosed in which a motor drive unit can be downsized and durability can be improved.

DETAILED DESCRIPTION

Hereinafter, each embodiment according to the present invention will be described in detail with reference to the accompanying drawings.

Since the exemplary embodiments described below are preferred specific examples according to the present disclosure, there are various limitations, which are technically preferable. However, in the following description, unless otherwise described to limit the present invention, the scope of the present invention is not limited to the exemplary embodiments.

An imaging apparatus for diagnosis according to an embodiment has an IVUS function and an OCT function.

Figure 1:
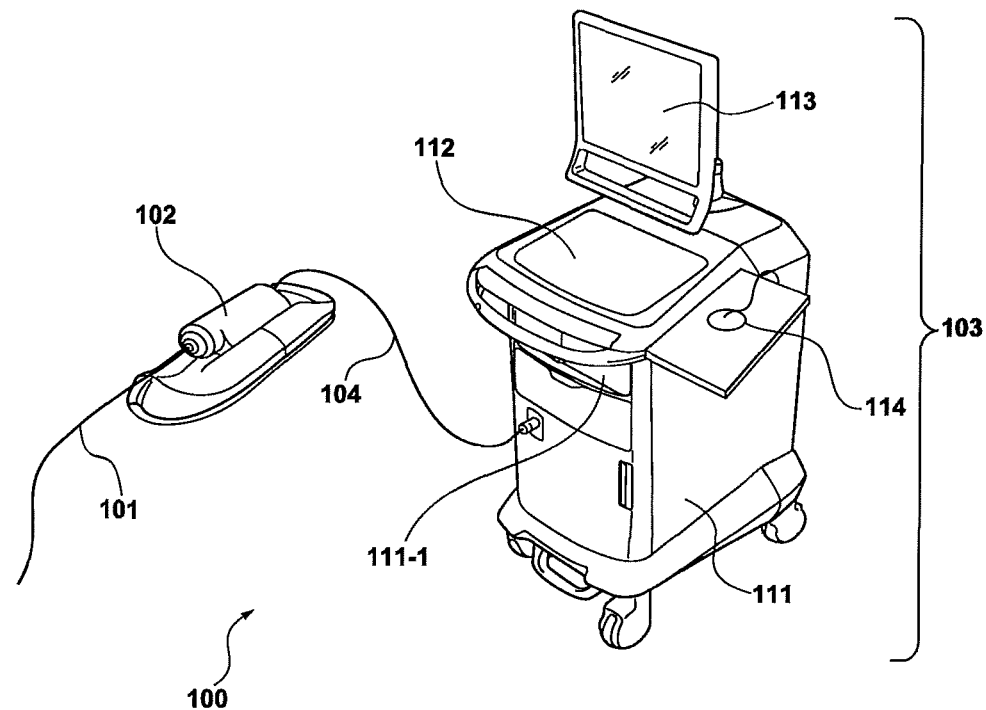
FIG. 1 is a view illustrating an external configuration of an imaging apparatus for diagnosis according to an exemplary embodiment.

FIG. 1 is a view illustrating an external configuration of an imaging apparatus for diagnosis 100 according to the embodiment.

As illustrated in FIG. 1, the imaging apparatus for diagnosis 100 includes a catheter 101, a motor drive unit (hereinafter, referred to as an MDU) 102, and an operation control device 103. The MDU 102 and the operation control device 103 are connected to each other via a cable 104 accommodating a signal line and an optical fiber.

In the operation control device 103, the reference numeral 111 represents a main body control unit.

The main body control unit 111 generates line data extending from a rotation center position in a radial direction, based on a signal (a reflected wave of an ultrasound wave emitted toward a vascular tissue and a reflected wave of light) obtained by an imaging core accommodated inside the catheter 101.

Then, through an interpolation process of the line data, a vascular tomographic image having each property is generated based on the ultrasound wave and optical interference.

The reference numeral 111-1 represents a printer & DVD recorder, which prints a processing result in the main body control unit 111 or stores the processing result as data.

In accordance with an exemplary embodiment, a storage destination of the processing result may be a server or a USB memory, and a type of the storage destination is not limited.

The reference numeral 112 represents an operation panel. A user inputs various setting values and instructions via the operation panel 112.

The reference numeral 113 represents a monitor (LCD) serving as a display device, which displays various tomographic images generated in the main body control unit 111.

The reference numeral 114 represents a mouse serving as a pointing device (coordinate input device).

The catheter 101 is directly inserted into a blood vessel.

Then, the catheter 101 has a structure for accommodating a rotatable imaging core, which is movable in the longitudinal direction.

In accordance with an exemplary embodiment, a distal end of the imaging core is provided with a housing for accommodating an ultrasound transceiver which generates an ultrasound wave, based on a signal transmitted from the imaging apparatus for diagnosis 100 and which receives and converts the ultrasound wave reflected from a vascular tissue into an electric signal, and an optical transceiver which continuously transmits transmitted light (measurement light) into the blood vessel and which continuously receives the light reflected from the inside of the blood vessel.

Then, a drive shaft for transmitting rotation force and moving force of the imaging core from the MDU 102 is connected to the housing.

That is, the imaging core can be configured to include the housing and the drive shaft.

In the imaging apparatus for diagnosis 100, the catheter 101, which accommodates the imaging core, is used so as to measure an internal state of the blood vessel.

The MDU 102 has a portion engaging with a connection portion in a proximal end of the catheter 101. In a state of being connected to the catheter 101, the MDU 102 functions as a relay device between the ultrasound transceiver and the optical transceiver in the imaging core inside the catheter 101, and the operation control device 103.

In addition, the MDU 102 drives a built-in motor. In this manner, the MDU 102 performs a process of pulling a hand-side inner tube and the drive shaft from a hand-side outer tube of the catheter 101, and controls the rotation of the drive shaft.

In addition, various switches and buttons are disposed in the MDU 102, and a user (physician) operates the switches and the buttons, thereby enabling the imaging core inside the catheter 101 to be rotationally driven and pulled back (movement of the imaging core).

Although a pull-back scanning process for an actual patient's blood vessel is well known, the process will be briefly described herein.

While viewing an X-ray image, the user confirms whether the distal portion of the catheter 101 moves to a diagnosis target position.

Then, the user operates the MDU 102 to instruct the pull-back process.

As a result, while the housing located in the distal end inside the catheter 101 and accommodating the ultrasound transceiver and the optical transceiver is rotated, the housing moves along the inside of the blood vessel.

The ultrasound transceiver transmits and receives the ultrasound wave, for example, 512 times during one rotation, and transmits the received signal to the operation control device 103 via the MDU 102.

The operation control device 103 receives this signal, and performs a predetermined arithmetic process, thereby obtaining line data having 512 lines extending in the radial direction from the rotation center of the transceiver.

The lines of the line data are close to each other at the rotation center position, and are farther from each other as the lines are separated from the rotation center.

Therefore, in order to obtain a two-dimensional image viewed by a human being, the operation control device 103 performs an interpolation process between the respective lines so as to generate a pixel between the lines.

As a result, a vascular tomographic image (ultrasound tomographic image) in a direction orthogonal to the axial direction of the blood vessel can be generated.

Similarly to the ultrasound transceiver, the optical transceiver emits the light and receives the light reflected from the vascular tissue, for example, 512 times during one rotation, and transmits the received light (measurement light) to the operation control device 103 via the MDU 102.

Therefore, the optical fiber is accommodated inside the drive shaft in the imaging core, and the optical transceiver and the operation control device 103 are optically connected to each other via the MDU 102.

The operation control device 103 causes a photo coupler to combine the measurement light emitted from the optical transceiver and reference light passing through a length known in advance with each other so as to generate interference light.

Then, the interference light is converted into digital data via a photo-detector and an A/D converter.

The obtained digital data is subjected to the fast Fourier transform so as to obtain the line data.

The subsequent process is almost the same as that of the ultrasound transceiver, and the interpolation process is performed so as to generate the vascular tomographic image (optical coherence tomographic image) of a plane orthogonal to the blood vessel axis.

The vascular tomographic images at the position on the blood vessel axis are combined with each other each time that the ultrasound transceiver is rotated once. In this manner, a three-dimensional image of the blood vessel can be generated using the ultrasound wave.

In addition, the vascular tomographic images at the position on the blood vessel axis are combined with each other each time that the optical transceiver is rotated once. In this manner, a three-dimensional image of the blood vessel can be generated using the optical interference.

A physician diagnoses a patient's blood vessel, based on the image obtained through this scanning.

The above-described configuration briefly shows the operation at the time of the pull-back scanning process according to the embodiment.

Next, the catheter 101 according to the embodiment will be described with reference to FIG. 2.

Figure 2:
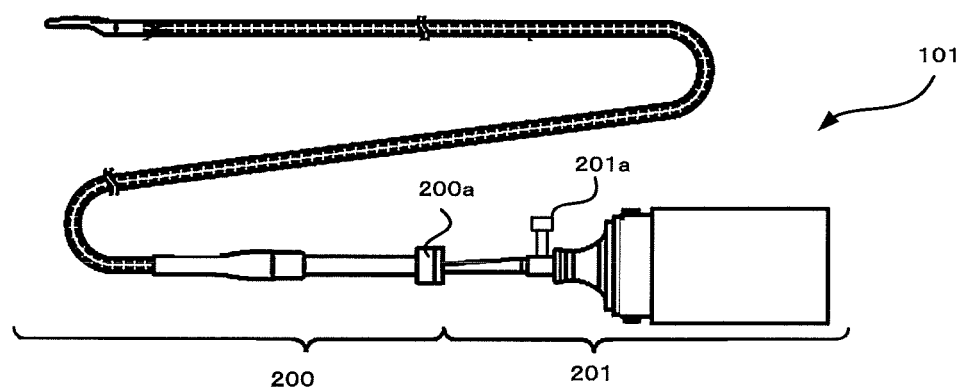
FIG. 2 is a view illustrating a structure of a catheter according to the exemplary embodiment.

FIG. 2 illustrates an external configuration diagram of the catheter 101.

The catheter 101 is configured to include an outer tube sheath 200 and an inner tube 201 accommodated inside the outer tube sheath 200 and inserted so as to be freely movable in the delivery direction.

In addition, a latch section 200a is disposed in or near the rear end of the outer tube sheath 200, and the latch section 200a is fixedly supported by the MDU 102.

In addition, in a state where the rear end portion of the inner tube 201 is gripped, the MDU 102 performs an operation of pulling the inner tube 201 in the illustrated rightward direction, and an operation of rotating the drive shaft interlocked inside the inner tube 201.

In FIG. 2, the reference numeral 201a represents a priming port (inlet port of a liquid (generally, a saline solution) for discharging air inside the outer tube sheath 200 and the inner tube 201).

Figure 3:
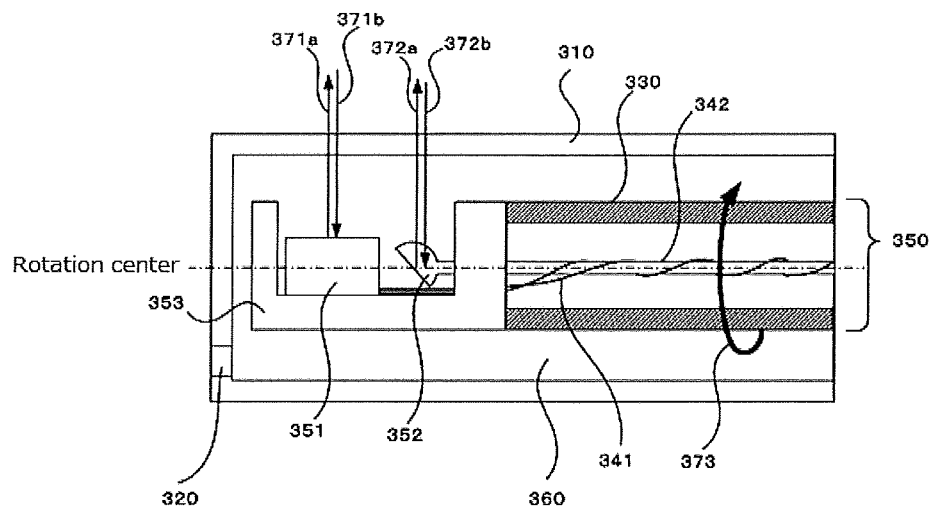
FIG. 3 is a cross-sectional view of a structure of a distal portion of the catheter according to the exemplary embodiment.

FIG. 3 illustrates a cross-sectional structure of a distal portion (side inserted into the blood vessel) of the catheter 101 according to the embodiment.

The inner tube 201 is inserted into the outer tube sheath 200.

In a sheath 310 in the outer tube sheath 200, at least a distal portion of the sheath 310 is configured to include a transparent material for maintaining light permeability.

In addition, the distal end of the sheath 310 is provided with a priming hole 320 for discharging air bubbles inside the outer tube sheath 200 and the inner tube 201 and filling the inside of the sheath with the priming solution.

In a case of the OCT, even if an optical path medium is air, the optical coherence tomographic image is less affected when the optical coherence tomographic image is constructed.

However, if the air is present on a propagation path of the ultrasound wave, there is a big acoustic impedance difference between the air and a material of the catheter sheath or the blood. Accordingly, before the ultrasound wave reaches a biological tissue, the ultrasound wave is reflected on the sheath or the blood interface. Consequently, sufficient energy for capturing the image does not permeate the biological tissue.

Therefore, the ultrasound wave can be diffused, and attenuates greatly.

It is assumed that the inner tube 201 according to the embodiment is used not only for the OCT but also for the IVUS. Accordingly, the priming hole 320 for discharging the air outward is provided.

The illustrated reference numeral 360 represents the priming solution injected from the priming port 201a in FIG. 2.

In addition, an imaging core 350 which is rotatable along an arrow 373 illustrated in the drawing is accommodated inside the sheath 310.

In accordance with an exemplary embodiment, the distal end of the imaging core 350 is provided with an ultrasound transceiver 351, an optical transceiver 352, and a housing 353 for accommodating both of these.

In addition, the housing 353 is supported by a drive shaft 330.

The drive shaft 330 is made of a flexible material, and has such a characteristic that the rotation can be satisfactorily transmitted from the MDU 102. For example, the drive shaft 330 is configured to include multiplex/multilayer close contact coils made of a metal wire such as stainless steel.

The drive shaft 330 has substantially the same length as that of the inner tube 201.

In addition, a signal line cable 341 electrically connected to the ultrasound transceiver 351 and a single mode fiber 342 optically connected to the optical transceiver 352 are disposed in the longitudinal direction inside the drive shaft 330.

The ultrasound transceiver 351 is provided so that the imaging core 350 according to the embodiment functions as the IVUS, and transmits the ultrasound wave toward an arrow 371a in accordance with a signal applied from the signal line cable 341. In a case where a reflected wave 371b is received from the vascular tissue, the ultrasound transceiver 351 transmits the received ultrasound wave to the MDU 102 (finally, to the operation control device 103) via the signal line cable 341, as an electric signal.

When the ultrasound transceiver 351 is inserted into and scans the blood vessel, the drive shaft 330 and the imaging core 350 are rotated along the arrow 373. Accordingly, the ultrasound transceiver 351 repeatedly transmits and receives the ultrasound wave within a plane orthogonal to the rotation axis.

As a result, the tomographic image orthogonal to the blood vessel axis can be obtained.

In accordance with an exemplary embodiment, the optical transceiver 352 is provided so that the imaging core 350 according to the embodiment functions as the OCT, and is configured to include a mirror having an inclination angle of approximately 45 degrees with respect to the illustrated rotation central axis, and a hemispherical ball lens.

The light guided via the single mode fiber 342 is reflected on the mirror in a direction of approximately 90 degrees with respect to the traveling direction, and is emitted toward the vascular tissue indicated by an arrow 372a via the lens.

Then, the light (arrow 372b) reflected from the vascular tissue is transmitted via the lens, and this time, the light is transmitted toward the MDU 102 (finally, to the operation control device 103) via the single mode fiber 342.

During the scanning, the imaging core 350 is rotated. In this manner, similarly to the IVUS, data for reconstructing the vascular tomographic image can be acquired.

A characteristic point of the present embodiment is a structure connected to (the inner tube 201 of) the catheter 101 in the MDU 102.

Therefore, first, a structure of the rear end portion connected to the MDU 102 of the catheter 101 will be described, and thereafter, a structure of the connection portion of the catheter 101 according to the embodiment will be described.

Figure 4A:
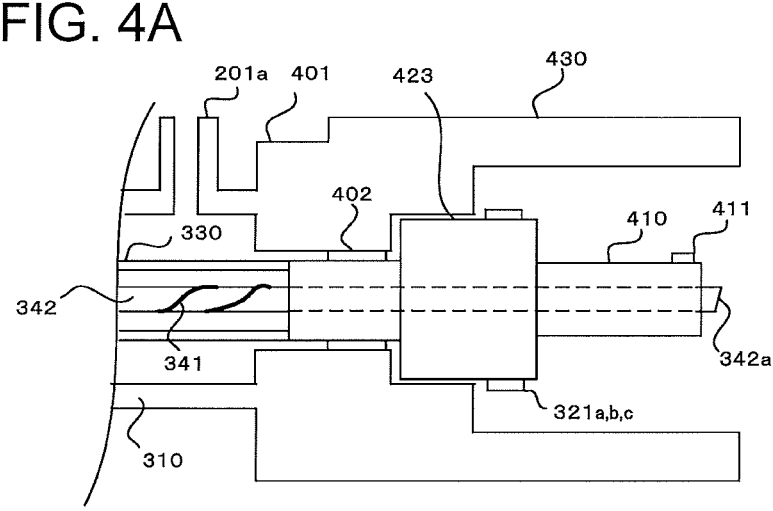
FIGS. 4A and 4B are views illustrating a structure of a rear end portion (side connected to an MDU) of the catheter according to the exemplary embodiment.

FIG. 4A illustrates a cross-sectional structure diagram of a connector unit of a rear end portion 401 (end portion connected to the MDU 102) of the inner tube 201 of the catheter 101.

Figure 4B:
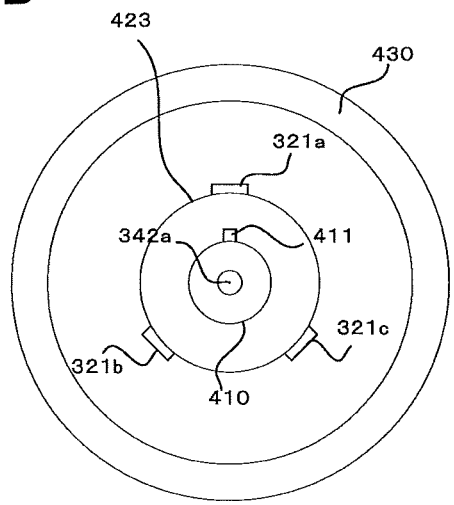

Then, FIG. 4B is a front view of the connector unit of the inner tube 201 when viewed from the MDU 102 side.

It should be noted that the illustration is simplified or partially omitted.

First, referring to FIGS. 4A and 4B, the structure of the rear end portion 401 of the inner tube 201 according to the embodiment will be described.

A first cylindrical member 410 having a circular cross section is supported by the rear end of the drive shaft 330.

The first cylindrical member 410 is rotatably supported via the rear end portion 401 and a rubber packing 402.

Accordingly, friction is decreased on a surface of a location in contact with at least the rubber packing 402 in the first cylindrical member 410.

In this manner, a liquid-tight state is maintained between the rear end portion 401 and the first cylindrical member 410.

In addition, the first cylindrical member 410 grips the fiber 342 so as to be fixed to the central axis, and the end portion of the fiber 342 is exposed as a fiber end 342a.

In addition, the first cylindrical member 410 is provided with a projection portion 411 in one place on the distal side surface.

In addition, the first cylindrical member 410 is fixed to a second cylindrical member 423 for suppressing deflection of the rotation axis and having the same diameter as or larger than the diameter of the first cylindrical member 410 (an integral structure may be used).

Then, the second cylindrical member 423 is rotatably supported by the rear end portion 401.

As a result, the fiber 342 is supported by the rear end portion 401 so that the center serves as the rotation axis.

Electrodes 321a to 321c (three poles) for being electrically connected to the ultrasound transceiver 351 of the imaging core 350 are disposed at an equal interval on a side surface of the second cylindrical member 423.

The electrodes 321a to 321c may have any structure as long as all of these are electrically connected to the electrodes on the MDU 102 side when the rear end portion of the inner tube 201 is inserted into and connected to the MDU 102.

In the embodiment, the electrodes 321a to 321c are metal plate springs, for example.

The reason that the electrodes 321a to 321c are disposed at the equal interval is as follows. The position of the center of gravity of the imaging core 350 including the first and second cylindrical members 410 and 423 is caused to substantially coincide with the center position of the fiber 342. In this manner, the center is no longer biased, and stable rotation is obtained.

In addition, the electrode is not limited to the plate spring. For example, the catheter side may employ a pin electrode, and the MDU side may employ a socket pin electrode, which receives the pin electrode.

As illustrated, the end surface of the fiber end 342a exposed from the first cylindrical member 410 is not only perpendicular to the axial direction but also inclined as large as a predetermined angle θ.

Similarly, the end surface of the fiber accommodated in the MDU 102 is perpendicular, and has a slope having the same angle θ so as to be planarly connected to the fiber end surface 342a.

In accordance with an exemplary embodiment, the reason that both the fiber end surfaces do not have only 90 degrees with respect to the axis but also the inclination angle θ is to reduce the influence of the light reflected on that connection surface.

The configuration is adopted as described above. Accordingly, when (the inner tube 201 of) the catheter 101 having the inclined optical fiber end surface is mounted on the MDU 102 in order to further reduce the influence of the reflected light, the respectively inclined fiber end surfaces need to be planarly connected to each other. More precisely, both of these need to be planarly connected to each other so that the phases are not shifted with respect to the rotation direction.

That is, the first cylindrical member 410 has to be connected to the MDU 102 in a determined orientation.

Therefore, the distal portion of the first cylindrical member 410 is provided with the projection portion 411, and the MDU 102 is provided with a guide groove, which guides the projection portion 411 (to be described in detail later).

Each of the electrodes 321a to 321c (three poles in the embodiment) disposed in the second cylindrical member 423 has the inherent properties of the electrode (one is ground, and the other remaining two are the electrodes for transmitting and receiving the ultrasound wave).

That is, the electrodes 321a to 321c have to be electrically connected to the respectively corresponding correct electrodes disposed in the MDU 102.

The second cylindrical member 423 is formed integrally with the first cylindrical member 410.

Therefore, when the inner tube 201 of the catheter 101 is mounted on the MDU 102, the fiber end surfaces are planarly connected to each other, and both of these enable the intended electrodes to be electrically and correctly connected to each other.

Hitherto, the structure of the portion connected to the MDU 102 in the inner tube 201 of the catheter 101 according to the embodiment has been described.

Figure 5A:
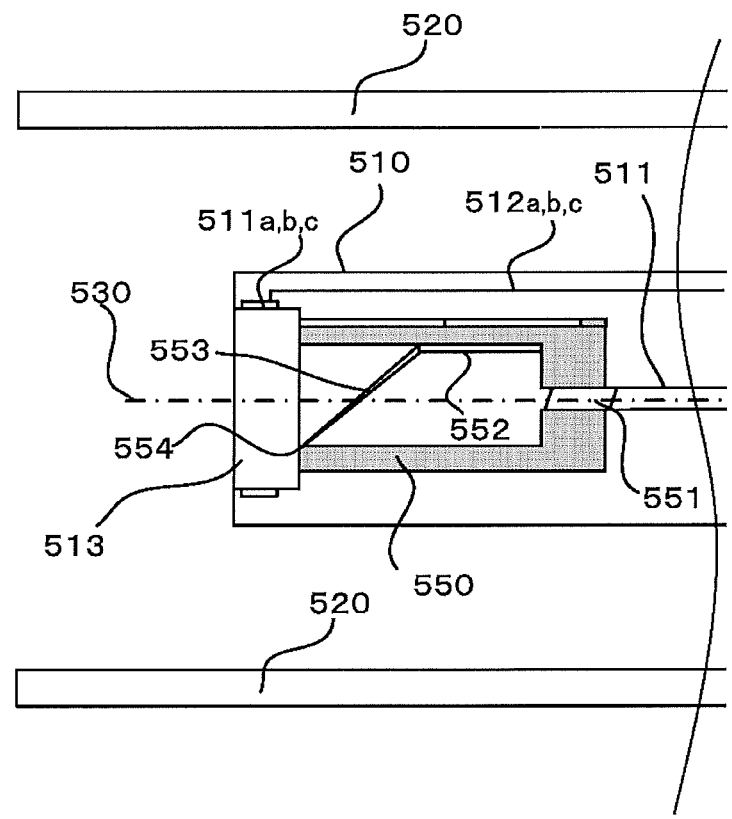
FIGS. 5A and 5B are views illustrating a structure and a connection state of a portion connected to the catheter in the MDU according to the exemplary embodiment.
Figure 5B:
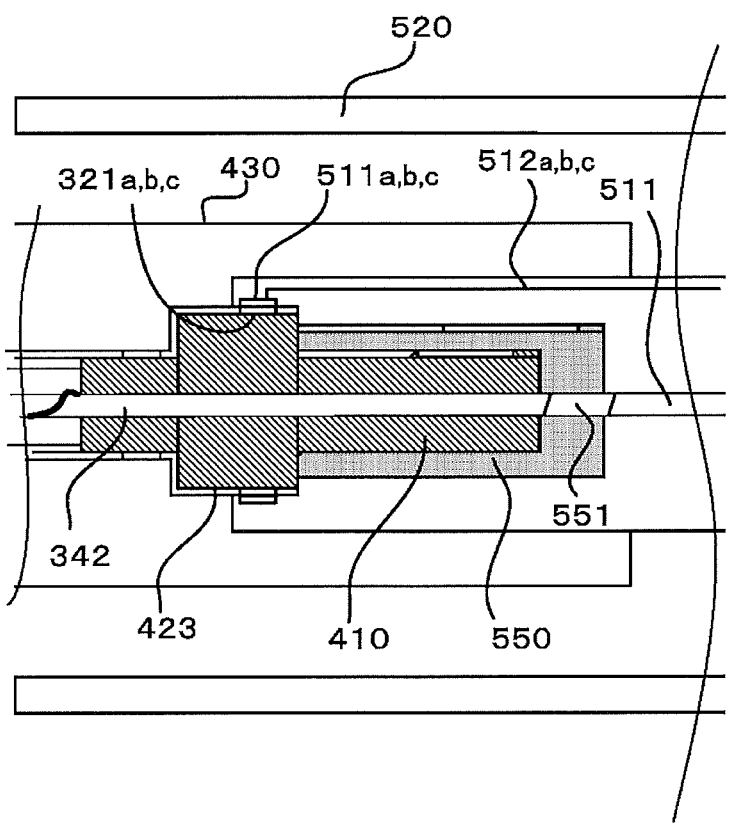

FIG. 5A is a partial cross-sectional view of the connector unit connected to the inner tube 201 of the catheter 101 in the MDU 102 according to the embodiment, and FIG. 5B is a cross-sectional view illustrating a state of being connected to the catheter 101.

The MDU 102 is provided with a connector unit 510 which rotates around an illustrated one-dotted chain line 530 as a rotation axis in accordance with a drive force from a drive motor belonging to the MDU 102.

The connector unit 510 is provided with an opening portion 513 for fitting (accommodating) the first cylindrical member 410 and the second cylindrical member 423 in the inner tube 201.

In addition, the MDU 102 has a cylindrical cover 520 for protecting the connector unit 510.

The inner surface of the opening portion 513 of the connector unit 510 is provided with electrodes 511a to 511c for being electrically connected to the electrodes 321a to 321c disposed in the second cylindrical member 423 when the catheter 101 is connected.

These electrodes 511a to 511c are disposed at an equal interval, similarly to the electrodes 321a to 321c.

Signal lines 512a to 512c connected to the electrodes 511a to 511c are accommodated in the connector unit 501, and are guided to the right hand side in the illustration.

In accordance with an exemplary embodiment, the connector unit 510 according to the embodiment accommodates a detachable adapter portion 550.

The adapter portion 550 has a cylindrical structure.

Figure 6A:
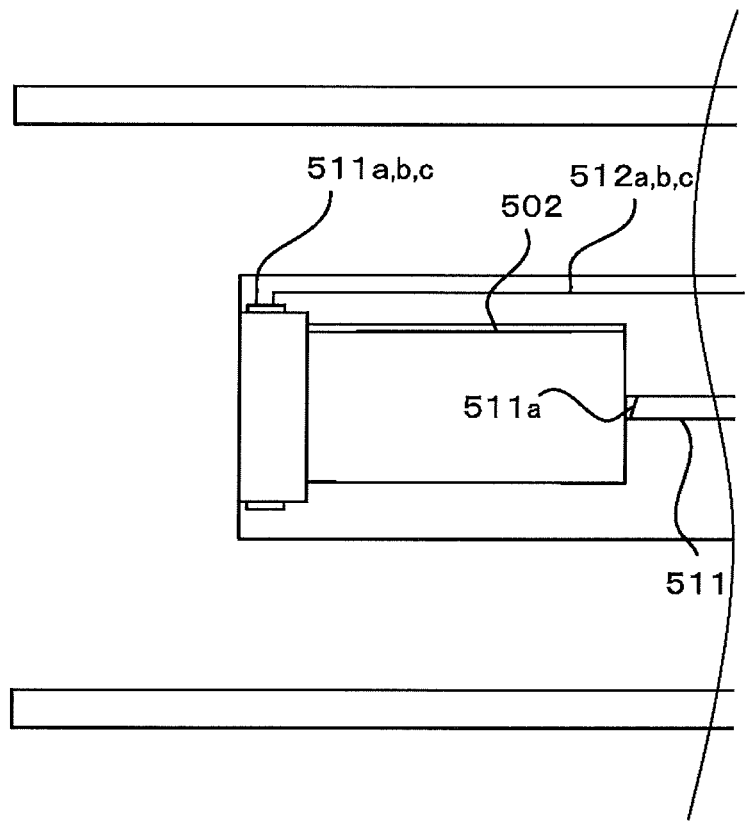
FIGS. 6A-6C are exploded views of the portion connected to the catheter in the MDU according to the exemplary embodiment.
Figure 6B:
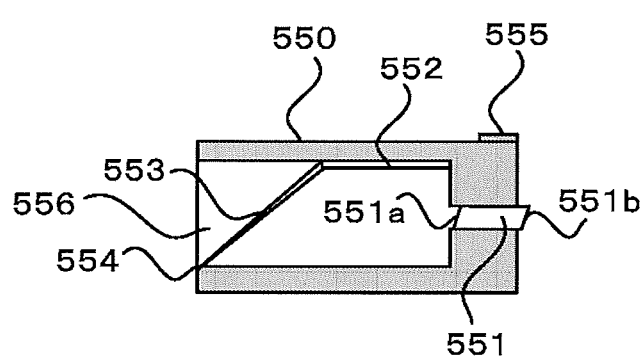

FIG. 6A illustrates a cross-sectional view of the connector unit 510 excluding the adapter portion 550, and FIG. 6B illustrates a cross-sectional view of the adapter portion 550.

A ferrule 551 is fixed to a surface opposite to the opening surface of the adapter portion 550.

Both end surfaces 551a and 551b of the ferrule 551 form a slope having an angle which is the same as that of the fiber end surface 342a in the catheter 101.

In accordance with an exemplary embodiment, the reason that the end surface 551a of the ferrule 551 in the adapter portion 550 is the slope having the angle which is the same as that of the fiber end surface 342a of the catheter 101 is that both of these are planarly connected to each other.

Therefore, the inner surface of the adapter portion 550 is provided with a guide groove 552 for guiding the projection portion 411 of the first cylindrical member 410 of the catheter 101.

In addition, it is desirable that a user simply inserts the catheter 101 into the MDU 102 without paying attention to the orientation of the catheter 101 (to be precise, the orientation of the first cylindrical member 410) so that the projection portion 411 of the first cylindrical member 410 is guided by the guide groove 552.

Therefore, in the adapter portion 550 according to the embodiment, a guide wall 553 for regulating the rotation direction of the projection portion 411 is disposed in a range from the opening surface to the guide groove 552.

Figure 6C:
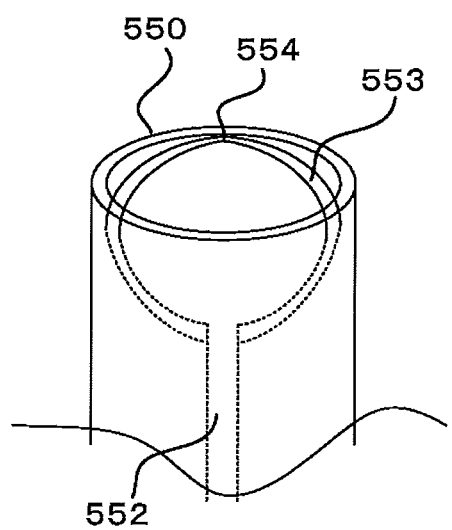

FIG. 6C illustrates a partially transparent perspective view of an opening portion 556 in the adapter portion 550.

As illustrated, a position closest to the opening surface is set to a vertex 554, and the guide wall 553 is disposed to be inclined along the both side surfaces. The guide groove 553 is located on a side opposite to the vertex 554.

The structure is employed as described above. Accordingly, when a user inserts the catheter 101 into the MDU 102, if the projection portion 411 of the first cylindrical member 410 is misaligned with the vertex 554 of the guide wall, the user can simply insert the catheter 101. Then, the inner tube 201 of the catheter 101 pivots, and finally, the fiber end surface 342a and the fiber end surface 551a of the adapter portion 550 can be planarly connected to each other.

In accordance with an exemplary embodiment, a case may happen where the projection portion 411 of the first cylindrical member 410 coincides with the vertex 554 of the guide wall when the user inserts the catheter 101 into the MDU 102.

However, in this case, the user may simply twist the catheter 101, for example, a little, and may insert the catheter 101 into the MDU 102. Accordingly, the user's operation can be simplified.

As described above, the fiber end surface 342a of the catheter 101 and the fiber end surface 551a of the adapter portion 550 can be planarly connected to each other.

On the other hand, the other fiber end surface 551b of the adapter portion 550 and the fiber end surface 551a extending from a rotating portion (not illustrated) of the MDU 102 in the connector unit 510 also need to be planarly connected to each other.

For this purpose, in accordance with an exemplary embodiment, when the adapter portion 550 is accommodated in the connector unit 510, the rotation direction of the adapter portion 550 has to be oriented in a direction regulated in advance.

Therefore, the adapter portion 550 according to the embodiment is provided with a projection portion 555 at a position of the outer side surface opposite to the opening portion.

Then, the inner side surface of the connector unit 510 is provided with a guide groove 502 for guiding the projection portion 555.

When replacing the adapter portion 550, the user can planarly connect the fiber surfaces to each other by merely performing an inserting operation after the projection portion 555 of a new adapter portion 550 is aligned with the guide groove 502.

A guide wall similar to the guide wall 553 of the adapter portion 550 may be disposed inside the connector unit 510.

Herein, the reason that the adapter portion 550 is interposed when the optical fiber is connected between the catheter 101 and the MDU 102 will be described.

The catheter 101 used for a single medical procedure can be discarded, for example, in order to prevent infectious disease.

Therefore, the catheter can be inserted into and removed from the MDU 102 as many times as the number of medical procedures.

Therefore, the fiber end surface on the MDU 102 side is connected to the fiber of the catheter many times. Consequently, the surface may be damaged, and the tomographic image inevitably becomes inaccurate due to the optical interference.

If there is damage, which is ignored on the surface, for example, once, the damage may lead to a serious situation where the cable 104 for connecting the MDU 102 and the operation control device 103 to each other has to be replaced.

According to the present embodiment, the adapter portion 550 described in the above embodiment is directly connected to the fiber end surface 342a inside the catheter 101.

Moreover, as illustrated in FIG. 6B, the adapter portion 550 includes the ferrule 551 without including the electrical signal line, and has a relatively simple configuration which can be exclusively made of a resin.

Therefore, even if the end surface 551a of the ferrule 551 is damaged, the adapter portion 550 can be replaced. In this manner, a relatively accurate optical connection can be restored.

In addition, when a new adapter portion 550 is mounted, the projection portion 555 can be aligned with and inserted into the guide groove 502. Alternatively, in a case where the guide wall is present, both of these can be correctly connected to each other by merely performing the inserting operation in accordance with the pivoting movement. Accordingly, burden on an operator can be reduced, for example, to a negligible extent.

Hitherto, the embodiment has been described. According to the above-described embodiment, when the catheter 101 is connected to the MDU 102, the center of the fiber 342 accommodated in the imaging core 350 inside the catheter 101 is held as the rotation central axis of the imaging core 350.

As a result, compared to a case where the center of the fiber 342 is misaligned with the rotation center position, the MDU 102 can have a more compact structure.

In addition, according to the embodiment, the user is allowed to perform the simple operation of inserting the catheter 101 into the MDU 102. In this manner, the catheter 101 and the optical fiber inside the MDU 102 can be accurately connected to each other, and the signal lines for ultrasound diagnosis can be correctly connected to each other.

Furthermore, according to the embodiment, the portion of the MDU 102 which is optically connected to the optical fiber inside the catheter has a relatively simple structure which does not include the electrical circuit and the signal line, and serves as the adapter portion 550 which can be replaced.

Therefore, the adapter portion 550 can be simply replaced, if necessary. In this manner, the optical connection between the catheter 101 and the operation control device 103 can be restored at low cost.

The present disclosure is not limited to the above-described embodiment, and various modifications and alterations can be made without departing from the spirit and scope of the present disclosure.

The detailed description above describes an imaging apparatus for diagnosis using a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis, the imaging apparatus comprising:
   a motor drive unit (MDU) configured to be connected to a catheter and configured to move and rotate an imaging core accommodated in the catheter along a longitudinal direction of the catheter, and to generate a vascular optical coherence tomographic image and an ultrasound tomographic image of a subject, based on a signal output from the catheter;
   a catheter connector configured to be connected to the MDU in the catheter, the catheter connector including a first cylindrical member configured to accommodate an optical fiber optically connected to an optical transceiver disposed in a distal end of the imaging core, and that holds the optical fiber while exposing an end portion of the optical fiber as a fiber end, a cylindrical-shaped second cylindrical member configured to be fixed to the first cylindrical member and having a plurality of connection terminals electrically connected to an ultrasound transceiver disposed in the distal end of the imaging core, and a connector unit that rotatably supports the first and second cylindrical members;
   a MDU connector configured to be connected to the catheter connector in the MDU, the MDU connector having a shape which accommodates the catheter connector in order to optically connect the optical fiber of the first cylindrical member and an optical fiber leading from the imaging apparatus for diagnosis to each other when the catheter connector is connected, and in order to connect the connection terminals and the electrical signal lines leading from the imaging apparatus for diagnosis to each other;
   the MDU configured to support a center position of the end portion of the optical fiber exposed from the first cylindrical member of the catheter, as a rotation center position of the imaging core;
   a projection portion configured to regulate a rotation direction is disposed in the first cylindrical member in the catheter; and
   wherein the MDU connector includes:
      a first hollow cylindrical portion having an opening portion configured to accommodate the first cylindrical member, and wherein the opening portion side of the first hollow cylindrical portion is provided with a first guide wall which regulates a sliding direction of the projection portion when the first cylindrical member enters the opening portion, and a first guide groove which is disposed as an end portion of the first guide wall so as to guide the projection portion in an entering direction in a case where the projection portion reaches a predetermined angle; and
      a second hollow cylindrical portion having an opening portion for accommodating the first hollow cylindrical portion, and wherein an inner surface of the second hollow cylindrical portion is provided with a second guide groove which guides a projection portion disposed on an outer surface of the first hollow cylindrical portion in order to accommodate the first hollow cylindrical portion at a preset angle.

2. The imaging apparatus for diagnosis according to claim 1,
   wherein in the second hollow cylindrical portion, a second guide wall for guiding the projection portion of the first hollow cylindrical portion to the second guide groove is disposed on the opening portion side of the second hollow cylindrical portion.

3. An imaging apparatus for diagnosis, the imaging apparatus comprising:
   a motor drive unit (MDU) configured to be connected to a catheter and configured to move and rotate an imaging core accommodated in the catheter along a longitudinal direction of the catheter, and to generate a vascular optical coherence tomographic image and an ultrasound tomographic image of a subject, based on a signal output from the catheter;
   a catheter connector configured to be connected to the MDU in the catheter, the catheter connector including a first cylindrical member that accommodates an optical fiber optically connected to an optical transceiver disposed in a distal end of the imaging core, and that holds the optical fiber while exposing an end portion of the optical fiber as a fiber end, a second cylindrical member that is fixed to the first cylindrical member and having a plurality of connection terminals electrically connected to an ultrasound transceiver disposed in the distal end of the imaging core, and a connector unit that rotatably supports the first and second cylindrical members;

a MDU connector configured to be connected to the catheter connector in the MDU, the MDU connector having a first hollow cylindrical portion which optically connects the optical fiber of the first cylindrical member and an optical fiber leading from the imaging apparatus for diagnosis to each other, and a second hollow cylindrical portion having a plurality of electrodes configured to be connected to the plurality of connection terminals of the second cylindrical member and which has an opening portion for accommodating the first hollow cylindrical portion;

a projection portion for regulating a rotation direction is disposed in the first cylindrical member in the catheter;

the first hollow cylindrical portion having an opening portion for accommodating the first cylindrical member, and the opening portion side of the first hollow cylindrical portion having a first guide wall which regulates a sliding direction of the projection portion when the first cylindrical member enters the opening portion, and a first guide groove which is disposed as an end portion of the first guide wall so as to guide the projection portion in an entering direction in a case where the projection portion reaches a predetermined angle; and wherein the first hollow cylindrical portion is attachable to and detachable from the second hollow cylindrical portion.

4. The imaging apparatus for diagnosis according to claim 3, wherein the second hollow cylindrical portion has an opening portion for accommodating the first hollow cylindrical portion; and wherein an inner surface of the second hollow cylindrical portion is provided with a second guide groove which guides a projection portion disposed on an outer surface of the first hollow cylindrical portion in order to accommodate the first hollow cylindrical portion at a preset angle.

5. The imaging apparatus for diagnosis according to claim 4, wherein in the second hollow cylindrical portion, a second guide wall for guiding the projection portion of the first hollow cylindrical portion to the second guide groove is disposed on the opening portion side of the second hollow cylindrical portion.

* * * * *